(12) United States Patent
Grijalva

(10) Patent No.: US 7,318,440 B1
(45) Date of Patent: Jan. 15, 2008

(54) EYE PATCH

(76) Inventor: Beth N. Grijalva, 111 E. Shadowpoint Cir., The Woodlands, TX (US) 77381

( * ) Notice: Subject to any disclaimer, the term of this patent is extended or adjusted under 35 U.S.C. 154(b) by 1577 days.

(21) Appl. No.: 09/594,445

(22) Filed: Jun. 15, 2000

(51) Int. Cl.
*A61F 9/00* (2006.01)

(52) U.S. Cl. ............................. 128/858; 2/13; 351/47; 351/48; 351/57; 351/58

(58) Field of Classification Search ................ 2/9, 2/13, 15; 351/47, 45, 158, 48, 57, 58; 128/846, 128/857, 858
See application file for complete search history.

(56) References Cited

U.S. PATENT DOCUMENTS

| 971,372 | A | * | 9/1910 | Hamilton |
| 1,310,077 | A | * | 7/1919 | Heaford |
| 1,709,195 | A | * | 4/1929 | Shindel |
| 1,720,548 | A | * | 7/1929 | Gilkerson |
| 2,172,573 | A | * | 9/1939 | Blumenthal |
| 2,668,952 | A | * | 2/1954 | Kobashikawa |
| 2,687,524 | A | * | 8/1954 | Mosher |
| 4,582,401 | A | * | 4/1986 | Grindle ..................... 351/45 |
| 5,389,066 | A | | 2/1995 | Rhame, Jr. |
| 5,402,189 | A | | 3/1995 | Gill |
| 5,900,921 | A | | 5/1999 | Min |
| 5,927,279 | A | | 7/1999 | Oviatt |

* cited by examiner

*Primary Examiner*—Lalita M. Hamilton
(74) *Attorney, Agent, or Firm*—Trop, Pruner & Hu, P.C.

(57) ABSTRACT

An eye patch that is usable with eyeglass frames includes a flexible body and at least one fastener. The fastener(s) fasten the flexible body to the front of the frames. The flexible body substantially blocks both frontal and peripheral vision of an eye of a wearer of the eyeglass frames.

54 Claims, 3 Drawing Sheets

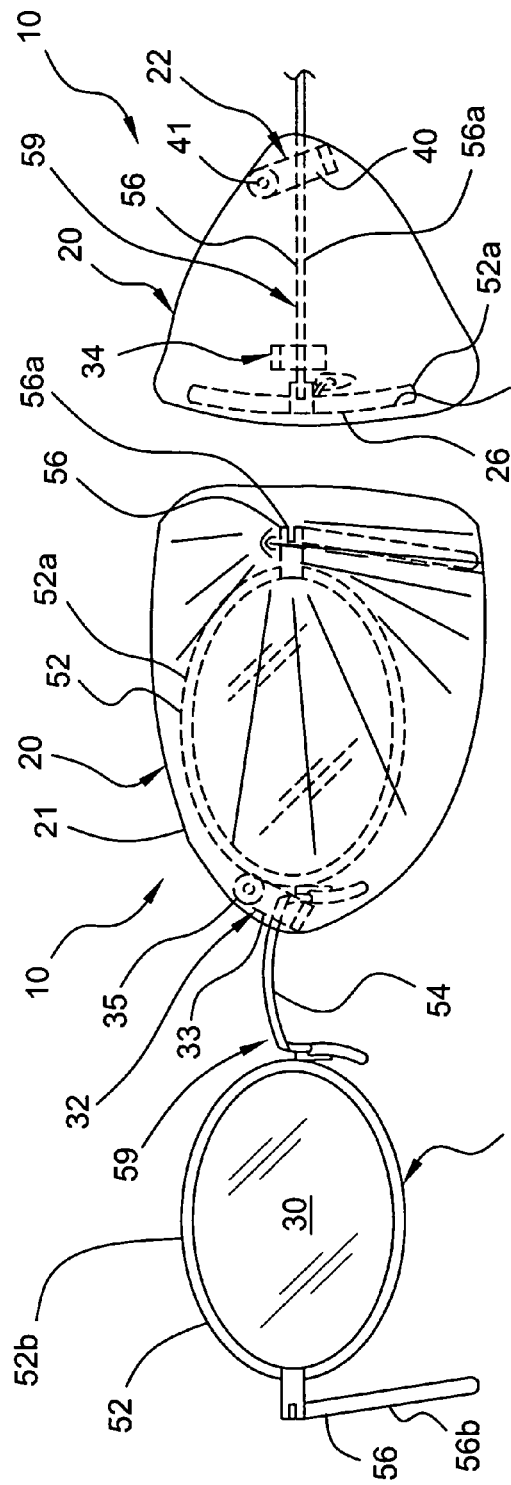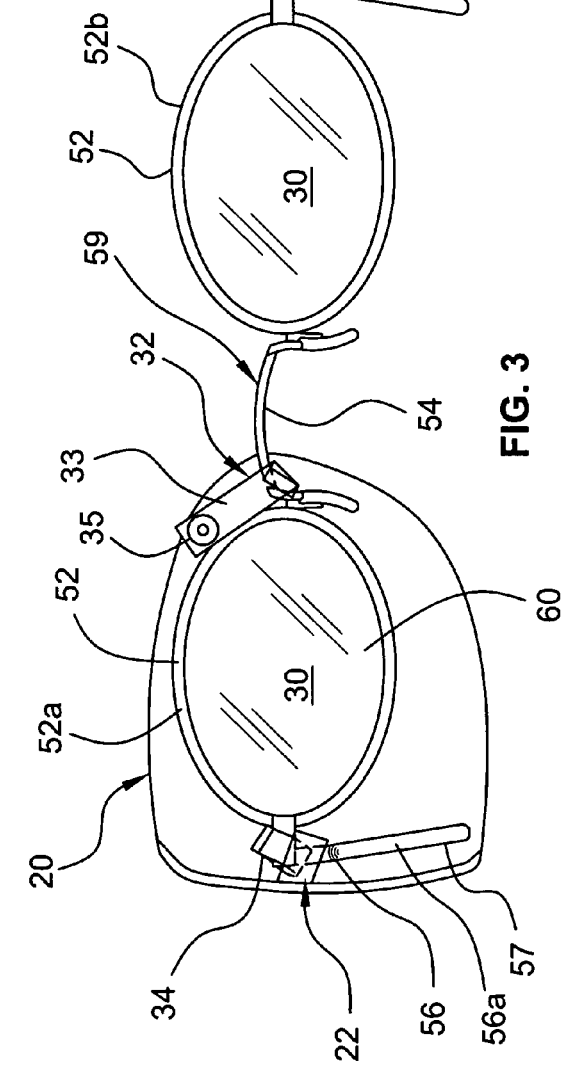

EYE PATCH

BACKGROUND

The invention generally relates to an eye patch.

It is not uncommon for one eye (called the dominant eye) to be substantially dominant with respect to the other eye (called the weaker eye). This imbalance typically worsens if left untreated and may even lead to loss of sight in the weaker eye. For a young child, the strength of the weaker eye may be improved by forcing reliance on the weaker eye. More specifically, the child may wear an eye patch to block the vision of the dominant eye and strengthen the muscles of the weaker eye.

One such eye patch is a disposable eye patch that has an adhesive strip for securing the eye patch to the child's face. However a difficulty with this arrangement is that the eye patch may cause irritation, thereby increasing the likelihood that the child may remove the patch. For example, the adhesive of the eye patch may cause irritation of the child's skin or eyebrow, and the proximity of the eye patch near the eye may also cause irritation. Furthermore, because the eye patch is disposable, the eye patch may need to be replaced on a daily basis or even more frequently, making use of the eye patch fairly expensive.

An alternative to the disposable adhesive eye patch is an eye patch that is attached to the inside of eyeglass frames, as described in U.S. Pat. No. 5,927,279. This patent describes an eye patch that is formed from a fabric body that is attached at one end to a nose pad of the eyeglass frames. The other end of the fabric body includes slots that receive an arm of the eyeglass frames. A difficulty with this eye patch is that the fabric body of the eye patch may contact and irritate the eye. Furthermore, repeatedly attaching the eye patch to the nose pad and removing the eye patch from the nose pad increases the likelihood that the nose pad may be broken, especially when performed by a child. Also this eye patch cannot be used with frames that do not have a certain type of nose pad.

Thus, there is a continuing need for an eye patch addressing one or more of the problems that are stated above.

SUMMARY

In an embodiment of the invention, an eye patch that is usable with eyeglass frames includes a flexible body and at least one fastener. The fastener(s) fasten the flexible body to the front of the frames. The flexible body substantially blocks both frontal and peripheral vision of the eye of a wearer of the eyeglass frames.

Other features and advantages of the invention will become apparent from the following description drawing and claims.

BRIEF DESCRIPTION OF THE DRAWING

FIG. 1 is a front view of an assembly that includes eyeglasses and an eye patch according to an embodiment of the invention.

FIG. 2 a side view of the assembly of FIG. 1 according to an embodiment of the invention.

FIG. 3 is a rear view of the assembly of FIG. 1 according to an embodiment of the invention.

DETAILED DESCRIPTION

Figure 4:
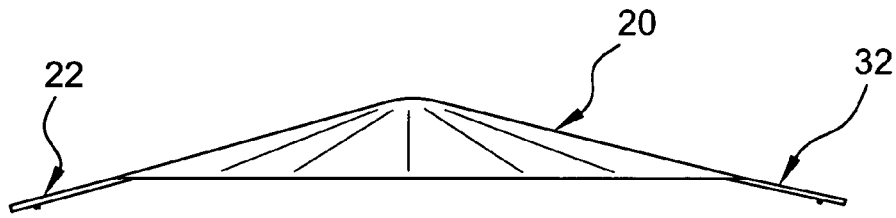
FIG. 4 is a top view of the eye patch of FIG. 1 according to an embodiment of the invention.

Referring to FIGS. 1 and 2, an embodiment 10 of an assembly in accordance with the invention includes a flexible eye patch 20 that is fastened to the front of a pair of eyeglasses 50 for purposes of blocking both the frontal and peripheral vision of an eye of a wearer of the eyeglasses 50. The blockage of the eye's vision may be used for purposes of strengthening the other eye, for example, to adjust the relative strengths of the wearer's eyes.

More specifically, in some embodiments of the invention, the eye patch 20 includes a substantially opaque and elongated flexible body 21 that is attached to eyeglass frames 59 of the eyeglasses 50 by at least two fasteners 22 (FIG. 2), and 32 (FIG. 1). The body 21 may be made from one or more layers of fabric that are singularly or collectively substantially opaque. The fabric may be, as examples, cloth or foam. When the body 21 is formed from multiple layers, these multiple layers may be laminated together by a fusible web or an adhesive, as just a few examples.

The fastener 22 (see FIG. 2), attaches one end of the body 21 to a side arm 56 (a left side arm 56*a*, for example), of the frames 59 approximately near the temple of the wearer, and the other fastener 32 attaches the other end of the body 21 to a bridge 54 of the frames 59. In this manner, when the eye patch 20 is fastened to the front of frames 59, the body 21 extends over a lens socket 52 (a left lens socket 52*a*, for example), of the frames 59 and extends around the side of the frames 59 to block both frontal and peripheral vision through the lens socket 52.

As depicted in FIGS. 1 and 2, the eye patch 20 extends around the left lens socket 52*a* (where the left/right orientation is with respect to the wearer of the eyeglasses 50). However, the eye patch 20 may alternatively extend over the right lens socket 52*b*, in other embodiments of the invention. In addition to the fasteners 22 and 32, the eye patch 20 may include additional fasteners, such as a fastener 34 (FIG. 2) to provide an attachment point closer to the left lens socket 52*a* than the attachment point that is provided by the fastener 22.

In the context of this application, the front of the eyeglasses 50 refers to the side (of the eyeglasses 50) that receives incident light from viewed objects when the pair of eyeglasses 50 is being worn. The rear of the eyeglasses 50 refers to the other side (of the eyeglasses 50) that is in close proximity to the face of the wearer. Although the pair eyeglasses 50 in the figures is depicted as including lens 30 that are inserted into the lens sockets 52*a* and 52*b*, one or both lens 30 may not be present in some embodiments of the invention.

The above-described arrangement may offer one or more of the following advantages. The eye patch 20 connects to the bridge 54, a feature common to all eyeglasses. In contrast, eye patches that connect to the inside of the frame via the nose pad may not be used in cases where nose pads are not present on the frames, such as plastic frames that are worn by many children, for example. Also, newer frames may have nose pads that are either molded into the frame or made in a continuous piece that does not permit attachment of the eye patch to the nose pad. Attachment of the patch to the bridge provides less risk of damaging the frames 59 when attaching or removing the eye patch 20. In this manner, many nose pads are attached using a wire that is soldered to or otherwise made a part of the frame itself, and the nose pads are not intended to bear stresses significantly greater than the weight of the eyeglasses resting on the wearer's nose. An individual, especially a child, could easily snap off a nose pad of this type in repeated applications and removals, thereby requiring replacement of the frames.

Connecting the eye patch 20 to the bridge 54 and fitting the eye patch over the lens socket 52 rather than around the lens socket 52 permits the eye patch 20 to fit a wide variety of sizes and shapes of lenses. Furthermore, fitting the eye patch 20 on the outside of the lens 30 rather than inside or inside and outside of the lens socket 52 provides a greater degree of comfort, making it more likely the wearer (especially when a child is the wearer), will find it easier to adapt to wearing the eye patch 20 and actually use it.

Attaching the eye patch 20 to the front of the frames 59 also gives better air circulation, less dampness and less potential irritation or infection of the skin or eye by the eye patch 20, moisture, dirt or by any detergents or cleaners used to launder the eye patch 20. Additionally, connecting the eye patch 20 to the front of the frames 59 means that the eye lashes and eye are not irritated by contact or rubbing.

The absence of an adhesive to attach the eye patch 20 directly to the face of the wearer prevents irritation of the skin and eyebrow from daily or more frequent application and removal, both from pulling and from sensitivities or allergies to the adhesive.

Because the eye patch 20 is attached to the front of the frames 59, the fabric of the body 21 may incorporate decorative designs and fabrics that are appealing to children and adults. In addition to keeping the eye patch 20 from rubbing or irritating the eye, attachment at the bridge 54 near the temple corner gives a greater stability in the fit that is especially important for active children. The eye patch 20 may be adapted (as described below) to form a universal patch that may be used on either the left or right eye. Durable materials may be used to form all parts of the eye patch 20, thereby allowing some form of cleaning and disinfecting of the eye patch 20 for repeated wearing.

Other and different advantages than those that are stated above are possible in the various embodiments of the invention.

Figure 5:
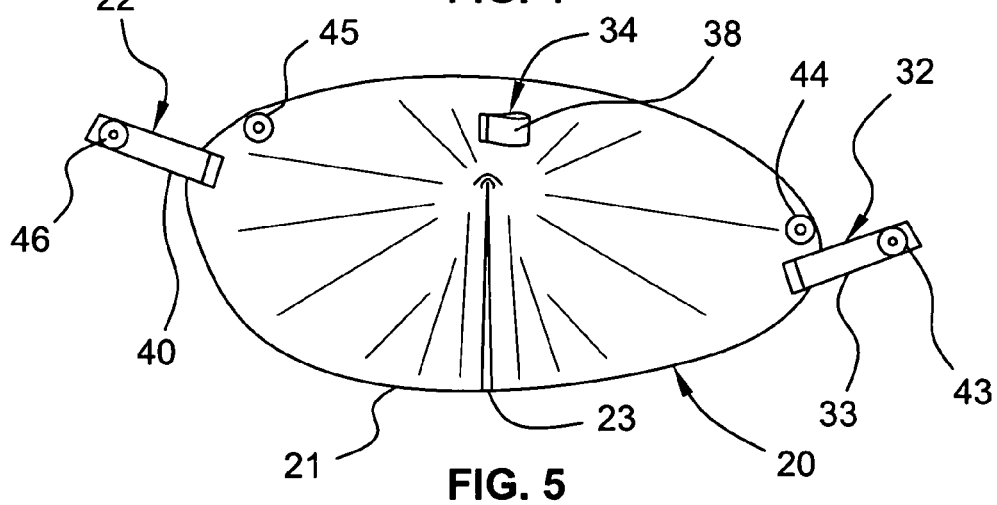
FIG. 5 is a rear view of the eye patch of FIG. 1 according to an embodiment of the invention.

FIG. 3 depicts a rear view of the eyeglasses 50. As shown, the fastener 32 includes a fabric loop 33 (a loop that is formed from a material that is sewn to the body 21, for example), that extends around the bridge 54 to secure the eye patch 20 to the front of the frames 59. The free end of the loop 33 is connected via a snap connector 35 to the body 21 to form a releasable connection that permits the fastener 32 to be attached to and removed from the bridge 54. Referring also to FIGS. 4 and 5, one end of the loop 33 is secured (sewn to, for example), to the body 21. The free end of the loop 33 includes one part 43 of the snap connector 35, with another mating part 44 of the snap connector 35 being secured to the body 21. The part 44 that is secured to the body 21 is positioned to allow sufficient slack in the loop 33 to permit the loop 33 to extend around the bridge 54 of the frames 59.

The fasteners 22 and 34 form loops around the side arm 56. In some embodiments of the invention, the fastener 22 includes a fabric loop 40 that has one end that is secured to the end of the body 21 opposite from the end of the body 21 that is attached to the fastener 32. The other free end of the loop 40 includes one part 46 of a snap connector 41 (see also FIG. 2), with another mating part 45 of the snap connector 41 being secured to the fabric body 21. The part 45 of the snap connector 41 is positioned to allow sufficient slack in the loop 40 to permit the loop 40 to extend around the left side arm 56a and to properly position the eye patch 20 on the frames 59.

The fastener 34, in some embodiments of the invention, is positioned approximately midway between the fasteners 22 and 32 on the body 20 to form an attachment point to the left side arm 56a near the left lens socket 52a. The fastener 34 includes a fabric loop 38 that has both of its ends attached together to the body 21. Therefore, the fastener 34 is essentially a permanent loop through which the left side arm 56a slides when the eye patch 20 is mounted on the frames 59. In some embodiments of the invention, the fabric loop 38 may be formed from an elastic material.

The fasteners 22, 32 and 34 are positioned on the body 21 to properly position the body 21 over the left lens socket 52a (see FIG. 1) and around the side of the frames 59 (see FIG. 2). For the example of the eye patch 20 that is depicted in FIG. 5, the fastener 22 is slightly higher than the fastener 32 to accommodate mounting the eye patch 20 over the left lens socket 52a.

Referring to FIG. 4, in some embodiments of the invention, the eye patch 20 may be generally cup-shaped for purposes of providing a contoured fit around the frames 59. The contoured shaped may be due to one or more darts 23 (one dart 23 is depicted in FIG. 5) that are formed in the body 21 near the lower part of the body 21. The term "dart" generally refers to feature that is created by a sewing technique in which a wedge-shaped piece of the body 21 is removed, and afterwards, the fabric that surrounds the region where the piece is removed is sewn together in a seam to impart the cup-shaped form to the body 21.

Figure 6:
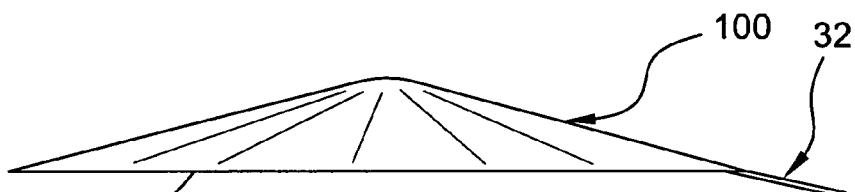
FIG. 6 is a top view of an eye patch according to another embodiment of the invention.
Figure 7:
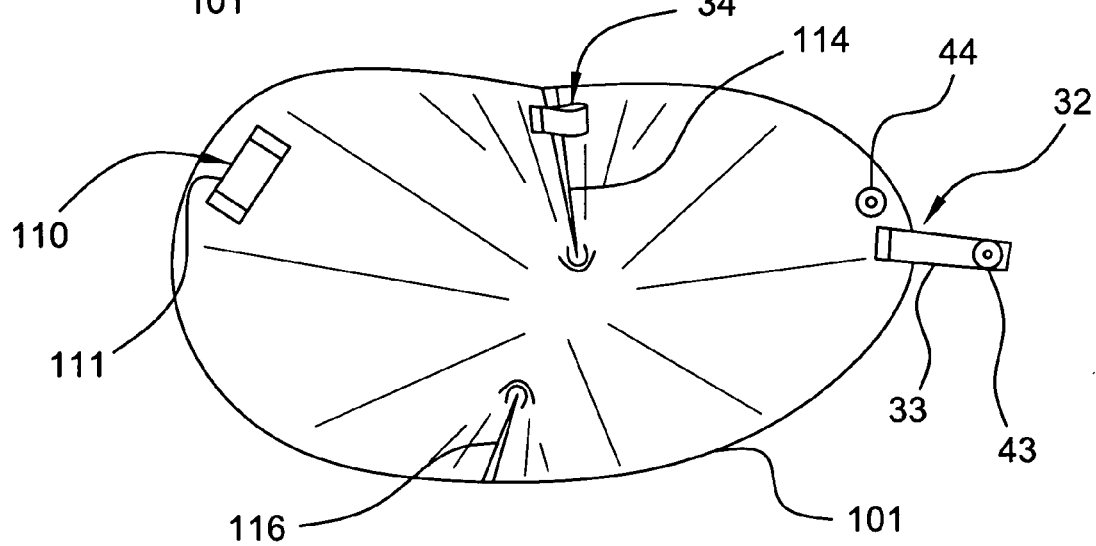
FIG. 7 is a rear view of the eye patch of FIG. 6 according to an embodiment of the invention.

Other embodiments are within the scope of the following claims. For example, FIGS. 6 (a top view) and 7 (rear view) depict a left eye patch 100 that may be used in place of the eye patch 20. The eye patch 100 has similar features to the eye patch 20, with the differences being pointed out below. In particular, for the eye patch 100, the fastener 22 (of the eye patch 20) is replaced by a fastener 110. The fastener 110 includes a fabric loop 111 that is attached (sewn to, for example) at its two ends to a body 101 of the eye patch 100. In this manner, the left side arm 56a of the frames 59 slides through the loop 111 to attach one end of the body 101 to the frames 59. Another difference between the two eye patches 20 and 100 is the presence of two darts 114 and 116 (as compared to the one dart 23 that is depicted for the eye patch 20) at the top and bottom of the eye patch 100 to increase the contoured fit of the eye patch 100 with the frames 59.

Figure 8:
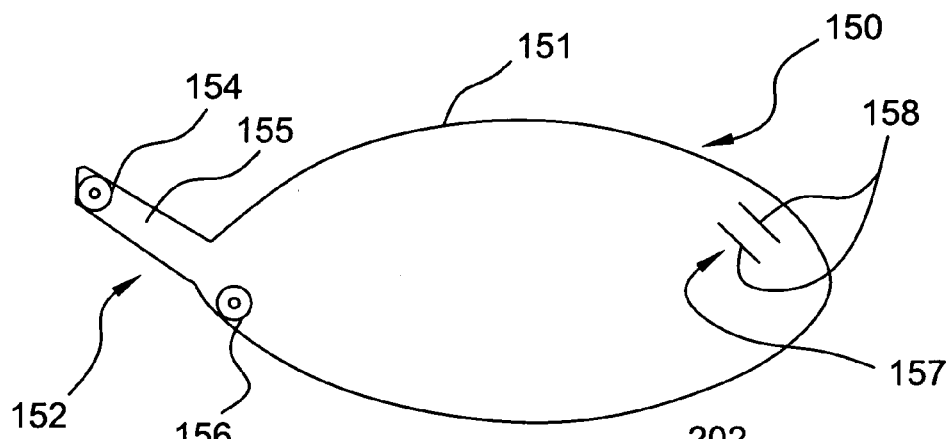
FIGS. 8, 9, 10 and 11 are rear views of eye patches according to different embodiments of the invention.

As another example, FIG. 8 depicts a right eye patch 150 that includes a fastener 157 for attaching one end of a flexible body 151 (of the eye patch 150) to the right arm 56b of the frames 59. Unlike the fasteners that are described above, the fastener 157 does not include a fabric loop that is formed from a piece of material that is separate from the body 151. Instead, the fastener 157 is formed from two parallel slits 158 that are formed in the body 151. In this manner, the right side arm 56b may be threaded through the slits 158 so that the fabric (of the body 151) that bridges the slits 158 holds the body 151 to the frames 59. A fastener 152 attaches the body 151 to the bridge 54. The fastener 152 may also be formed from the fabric that forms the body 151. In this manner, the body 151 has an extension 155 that forms a loop for extending around the bridge 54 to secure the other end of the body 151 to the frames 59. The far end of the extension 155 has a snap connector part 154 that mates with a complementary snap connector part 156 that is secured to the body 151 to form a releasable snap connector for attaching the eye patch 150 to the bridge 54.

Figure 9:
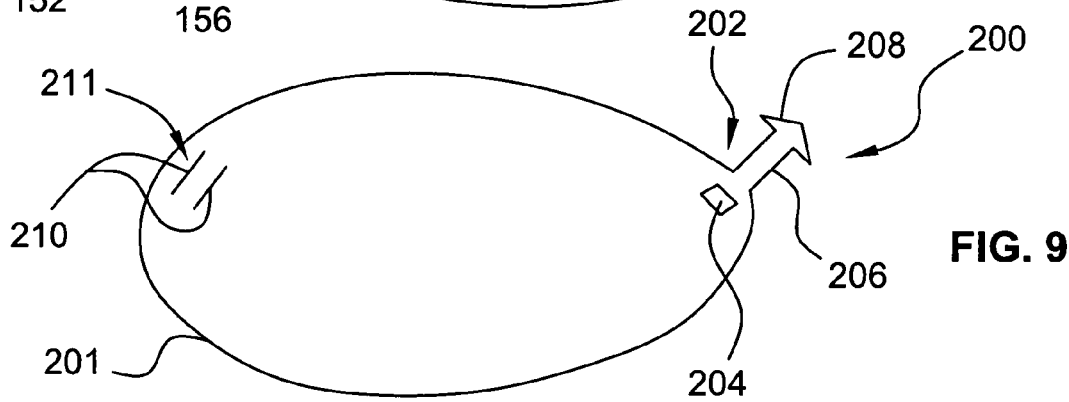

Referring to FIG. 9, in another embodiment of the invention, a left eye patch 200 includes a fastener 211 that is formed from slits 210 in a fabric body 201 (of the eye patch 200) for attaching the left side arm 56a of the frames 59 to one end of the body 201 similar to the fastener 157 that is formed from the slits 158, described above. The eye patch 200 also includes a fastener 202 for attaching the other end of the body 201 to the bridge 54. Unlike the fasteners that are described above, the fastener 202 includes an extension 206 with an arrowhead 208 formed at the tip of the extension 206. The arrowhead 208 may be inserted into a slot 204 (of the fastener 202) that is formed in the body 201. In this manner, when the arrowhead 208 is inserted into the slot 204, the extension 206 loops around the bridge 54, and the prongs of the arrowhead 208 extend beyond the front surface of the body 201 to releasably secure the arrowhead 208 to the body 201.

Figure 10:
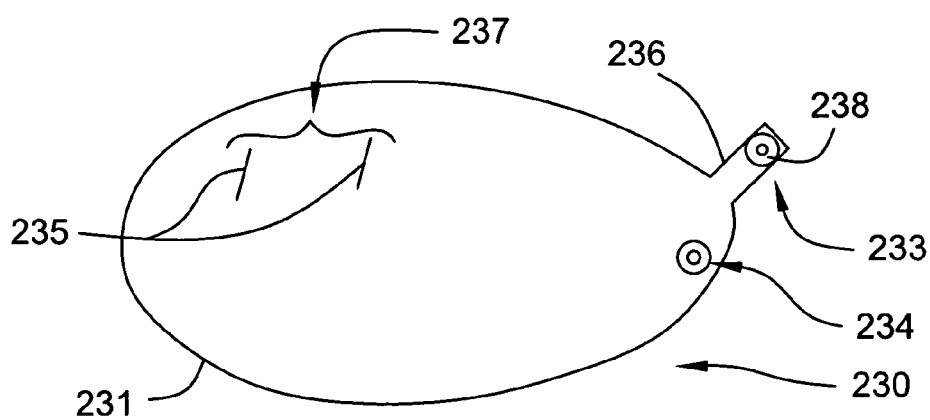

In yet another embodiment of the invention, FIG. 10 depicts a left eye patch 230 that includes a fastener 233 similar in design to the fastener 152 (see FIG. 8). In this manner, the fastener 233 includes an extension 236 from one end of a flexible body 231 (of the eye patch 230) to extend around the bridge 54. The free end of the fastener 233 includes a snap connector part 238 that mates with another snap connector part 234 that is attached to the body 231 to form a snap connection. The eye patch 230 also includes a connector 237 that is formed from two parallel slits 235 that receive the left side arm 56a that is threaded therethrough to attach the eye patch 230 to the left arm 56. It is noted that the slits 235 of the fastener 237 may be located farther apart than the slits 210 of the fastener 233.

Figure 11:
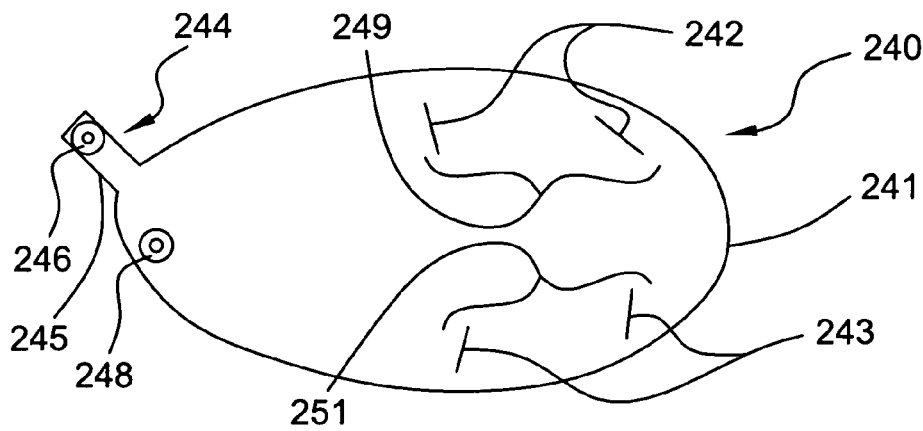

The eye patches depicted above are for use with either the left or right eye. However, universal eye patches are within the scope of the claims. For example, FIG. 11 depicts a universal eye patch 240 that may be used to block frontal and peripheral vision of either the left or right eye. In this manner, the eye patch 240 includes a fastener 244 for attaching the eye patch 240 to the bridge 54. This fastener 244 includes an extension 245 (of a body 241 of the eye patch 240) that extends from one end of the body 241 around the bridge 54. One end of the extension 245 includes a part 246 that mates with another part 248 that is attached to the body 241 to form a snap connection. Unlike similar fasteners that are described above, the fastener 244 may be used to attach the eye patch 240 to the bridge 54 regardless of whether the eye patch 240 covers the right or left eye. To accomplish this, the attached snap connector part 248 is located near the vertical midway point of the body 241 to permit its use regardless of the orientation of the eye patch 240.

The eye patch 240 includes two fasteners 249 and 251 to attach the eye patch 240 to the arm 56. More specifically, the fastener 249 is for the right eye configuration and includes two parallel slits 242 that are located near the top of the body 241 for the right eye configuration (depicted in FIG. 11) for purposes of attaching the eye patch 240 to the right side arm 56b. In this right eye configuration, two parallel slits 243 of the fastener 251 are formed in the body 241 near the bottom of the body 241. However, the fastener 251 is used for the left eye configuration. Therefore, when the eye patch 240 is flipped over to place the eye patch 240 in the left eye configuration, the slits 243 are located near the top of the body 241 in the proper position to attach the eye patch 240 to the left side arm 56a.

In the preceding description, directional terms, such as, "right," "left," "top," "bottom," etc., may have been used for reasons of convenience to describe eye patches, eyeglass frames and their associated components. However, such orientations are not needed to practice the invention, and thus, other orientations are possible and are within the scope of the claims.

Other embodiments are within the scope of the following claims. For example, other fasteners, such as hook and loop fasteners, may be used in other embodiments of the invention. Other types of materials may be used for the flexible body. The flexible body may assume other shapes. In some embodiments of the invention, the frames do not include lens sockets, but instead, the lens may be part of the frames. Other arrangements are possible.

While the invention has been disclosed with respect to a limited number of embodiments, those skilled in the art, having the benefit of this disclosure, will appreciate numerous modifications and variations therefrom. It is intended that the appended claims cover all such modifications and variations as fall within the true spirit and scope of the invention.

What is claimed is:

1. An eye patch usable with eyeglass frames that comprises a bridge and a side arm, the eye patch comprising:
   a flexible body to be positioned on a front of the frames to substantially block both frontal and peripheral vision of an eye;
   a first fastener to attach the body to the bridge; and
   a second fastener to attach the body to the side arm.

2. The eye patch of claim 1, wherein
   the body is adapted to at least partially extend over a lens socket of the eyeglass frames.

3. The eye patch of claim 1, wherein
   the body is adapted to at least partially extend over a lens of the eyeglass frames.

4. The eye patch of claim 1, wherein
   the body is adapted to at least partially extend along the side arm.

5. The eye patch of claim 1, wherein the first fastener comprises a loop comprising a first end secured to the body and a second end adapted to extend around the bridge to releasably couple the bridge to the body.

6. The eye patch of claim 5, wherein the first fastener further comprises:
   a releasable connector adapted to releasably couple the side arm to the body.

7. The eye patch of claim 5, wherein
   the body includes at least one slot, and
   the second end comprises a pronged tab adapted to be inserted into the slot to releasably couple the second end to the body.

8. The eye patch of claim 1, wherein the second fastener comprises at least one slit formed in the body to receive the arm.

9. The eye patch of claim 1, wherein the second fastener comprises:
   a loop adapted to extend around the side arm, the loop having a first end secured to the body and a second end.

10. The eye patch of claim 9, wherein the second end is adapted to releasably couple the loop to the body.

11. The eye patch of claim 9, wherein the second end is secured to the body.

12. The eye patch of claim 1, wherein the body comprises a fabric selected from a set consisting essentially of: fabric and foam.

13. The eye patch of claim 1, wherein the body comprises a pliable material.

14. The eye patch of claim 1, wherein the first fastener is adapted to attach the body to the bridge regardless of whether the eye comprises a left eye or a right eye.

15. The eye patch of claim 1, wherein the second fastener is adapted to attach the body to the arm regardless of whether the eye comprises a left eye or a right eye.

16. An assembly comprising:
   eyeglass frames comprising a bridge and a side arm; and
   an eye patch comprising:
   a flexible body to be positioned on a front of the frames to substantially block both frontal and peripheral vision of an eye;
   a first fastener to attach the body to the bridge of the eyeglass frames; and
   a second fastener to attach the body to the arm of the eyeglass frames.

17. The assembly of claim 16, wherein
   the eyeglass frames comprises a lens socket, and
   the body is adapted to at least partially extend over the lens socket.

18. The assembly of claim 16, wherein
   the body is adapted to at least partially extend along the side arm.

19. The assembly of claim 16, wherein the first fastener comprises a loop comprising a first end secured to the body and a second end adapted to extend around the bridge to releasably couple the bridge to the body.

20. The assembly of claim 19, wherein the first fastener further comprises:
   a releasable connector adapted to releasably couple the side arm to the body.

21. The assembly of claim 19, wherein
   the body includes at least one slot, and
   the second end comprises a pronged tab adapted to be inserted into the slot to releasably couple the second end to the body.

22. The assembly of claim 16, wherein the second fastener comprises at least one slot formed in the body to receive the side arm.

23. The assembly of claim 16, wherein the second fastener comprises:
   a loop adapted to extend around the side arm, the loop having a first end secured to the body and a second end.

24. The assembly of claim 23, wherein the second end is adapted to releasably couple the loop to the body.

25. The assembly of claim 23, wherein the second end is secured to the body.

26. The assembly of claim 16, wherein the body comprises a fabric selected from a set consisting essentially of: fabric and foam.

27. The assembly of claim 16, wherein the body comprises a fabric selected from a pliable material.

28. The assembly claim 16, wherein the first fastener is adapted to attach the body to the bridge regardless of whether the eye comprises a left eye or a right eye.

29. The assembly of claim 16, wherein the second fastener is adapted to attach the body to the side arm regardless of whether the eye comprises a left eye or a right eye.

30. An eye patch usable with eyeglass frames, comprising:
   a flexible body to be fastened to at least partially cover a front of the eyeglass frames to substantially block both frontal and peripheral vision of an eye; and
   at least one fastener to secure the flexible body to the frames, said at least one fastener comprising:
   a first fastener to attach the eye patch to a bridge of the eyeglass frames; and
   a second fastener to attach the eye patch to a side arm of the eyeglass frames.

31. The eye patch of claim 30, wherein
   the body is adapted to at least partially extend over a lens socket of the eyeglass frames.

32. The eye patch of claim 30, wherein
   the body is adapted to at least partially extend along a side arm of the frames.

33. An assembly comprising:
   eyeglass frames, comprising a side arm and a bridge; and
   an eye patch comprising:
   a flexible body to be fastened to at least partially cover a front of the eyeglass frames to substantially block both frontal and peripheral vision of an eye; and
   at least one fastener to secure the flexible body to the frames, said at least one fastener comprising:
   a first fastener to attach the eye patch to the bridge; and
   a second fastener to attach the eye patch to the side arm.

34. The assembly of claim 33, wherein
   the eyeglass frames comprises a lens socket, and
   the body is adapted to at least partially extend over the lens socket.

35. The assembly of claim 33, wherein
   the eyeglass frames holds a lens, and
   the body is adapted to at least partially extend over the lens.

36. The assembly of claim 33, wherein
   the body is adapted to at least partially extend along a side arm of the frames.

37. An eye patch usable with eyeglass frames that comprises a bridge, the eye patch comprising:
   a flexible body to be positioned on a front of the frames to substantially block both frontal and peripheral vision of an eye; and
   a fastener extending from the body to attach the body to the bridge.

38. The eye patch of claim 37, wherein
   the body is adapted to at least partially extend along a side arm of the frames.

39. The eye patch of claim 37, wherein the flexible body is not positioned on a rear of the frames.

40. The eye patch of claim 37, wherein the fastener comprises a tab separate from the body to secure the body to the bridge of the frame.

41. The eye patch of claim 37, wherein the fastener comprises a loop comprising a first end secured to the body and a second end adapted to extend around the bridge to releasably couple the bridge to the body.

42. The eye patch of claim 37, wherein the fastener comprises a releasable connector adapted to releasably couple the bridge to the body.

43. The eye patch of claim 37, wherein
   the body includes at least one slot, and
   the second end comprises a pronged tab adapted to be inserted into the slot to releasably couple the second end to the body.

44. An eye patch usable with eyeglass frames that comprises a bridge and a side arm, the eye patch comprising:
   a flexible body comprising a first portion positioned on a front of the frames to substantially block frontal vision of an eye and a second portion attached to the first portion to substantially block peripheral vision of the eye;

a first fastener to attach the body to the bridge; and a second fastener to attach the body to the side arm.

45. The eye patch of claim 44, wherein the first and second portions are substantially opaque.

46. The eye patch of claim 44, wherein the second portion is adapted to at least partially extend along the side arm.

47. The eye patch of claim 44, wherein the first fastener comprises a loop comprising a first end secured to the body and a second end adapted to extend around the bridge to releasably couple the bridge to the body.

48. The eye patch of claim 47, wherein the first fastener further comprises:

a releasable connector adapted to releasably couple the side arm to the body.

49. The eye patch of claim 44, wherein the second fastener comprises:

a loop adapted to extend around the side arm, the loop having a first end secured to the body and a second end.

50. A method comprising:

providing a flexible body to attach to a front of eyeglass frames to substantially block both frontal and peripheral vision of an eye;

providing a first fastener to attach the body to a bridge of the eyeglass frames; and providing a second fastener to attach the body to a side arm of the eyeglass frames.

51. The method of claim 50, further comprising:

forming the body to at least partially extend along the side arm of the eyeglass frames.

52. The method of claim 50, further comprising:

selecting a material for the flexible body, wherein the material is substantially opaque.

53. The method of claim 50, further comprising:

extending a loop around the bridge to attach the body to the bridge.

54. The method of claim 50, further comprising:

extending a loop around the side arm to attach the body to the side arm.

* * * * *